(12) United States Patent
Traverso et al.

(10) Patent No.: US 7,910,300 B2
(45) Date of Patent: Mar. 22, 2011

(54) DISEASE DETECTION BY PROTEIN TRUNCATION ASSAYS

(75) Inventors: C. Giovanni Traverso, Etobicoke (CA); Kenneth W. Kinzler, Bel Air, MD (US); Bert Vogelstein, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 314 days.

(21) Appl. No.: 11/703,821

(22) Filed: Feb. 8, 2007

(65) Prior Publication Data

US 2009/0117546 A1 May 7, 2009

Related U.S. Application Data

(63) Continuation of application No. 10/307,505, filed on Dec. 2, 2002, now abandoned.

(60) Provisional application No. 60/336,177, filed on Dec. 6, 2001.

(51) Int. Cl.
 *C12Q 1/68* (2006.01)
 *C12P 19/34* (2006.01)
 *G01N 33/53* (2006.01)
 *C07H 21/02* (2006.01)
(52) U.S. Cl. ............... 435/6; 435/7.1; 435/91.2
(58) Field of Classification Search .................. None
 See application file for complete search history.

(56) References Cited

U.S. PATENT DOCUMENTS 5,709,998 A 1/1998 Kinzler et al.

FOREIGN PATENT DOCUMENTS

WO WO-98/11249 3/1998
WO WO-01/09386 A2 2/2001

OTHER PUBLICATIONS

Kuster, B. et al., Current Opinion Struct. Biol., vol. 8, pp. 393-400 (1998).*
Deuter, R. et al., Human Mutat., vol. 11, pp. 84-89 (1998).*
Miyoshi, Y. et al., Hum. Mol. Genet., vol. 1, pp. 229-233 (1992).*
Giardello, F.M. et al., Gut, vol. 40, pp. 521-525 (1997).*
Ficari, F. et al., Brit. J. Cancer, vol. 82, pp. 348-353 (2000).*
M.J. Brisco et al., "Detection and Quantitation of Neoplastic Cells in Acute Lymphoblastic Leukaemia, by Use of the Polymerase Chain Reaction," British Journal of Haematology, 1991, 79, 211-217.
M. J. Brisco et al., "Outcome Prediction in Childhood Acute Lymphoblastic Leukaemia by Molecular Quantification of Residual Disease at the End of Induction," The Lancet, Jan. 22, 1994, vol. 343, pp. 196-200.

(Continued)

*Primary Examiner* — Teresa E Strzelecka
(74) *Attorney, Agent, or Firm* — Banner & Witcoff, Ltd.

(57) ABSTRACT

Genetic diseases can be diagnosed by detection of mutations in causative genes. Protein truncation assays can be used to detect gene products of truncation-type mutations. However, the sensitivity of the assays is often insufficient to detect mutations present in a sample of DNA at a low frequency. Sensitivity can be increased by dividing samples so that the signal generated by a mutant allele comprises a larger fraction of the total alleles than prior to dividing. Thus a previously undetectable signal generated by the mutant allele can become detectable in the assay. Such increased sensitivity permits detection at early stages and in samples having high levels of other alleles.

26 Claims, 6 Drawing Sheets

OTHER PUBLICATIONS

P. J. Sykes et al, "Quantitation of Targets for PCR by Use of Limiting Dilution," BioTechniques, 1992, vol. 13, No. 3, pp. 444-449.

Traverso, G. et al., "Detection of APC Mutations in Fecal DNA from Patients with Colorectal Tumors," *N. Engl. J. Med.*, Jan. 2002, vol. 346, pp. 311-320.

Van Der Luijt, R. et al., "Rapid Detection of Translation-Termination Mutations at the *Adenomatous Polyposis Coli* (APC) Gene by Direct Protein Truncation Test," *Genomics*. Mar. 1994, vol. 20, pp. 1-4.

Powell, et al., "Molecular Diagnosis of Familial Adenomatous Polyposis", New England Journal of Medicine, Dec. 30, 1993, 1982-1987, vol. 329, No. 27.

Gismondi, et al., "Characterization of 19 Novel and Six Recurring APC Mutations in Italian Adenomatous Polyposis Patients, Using Two Different Mutation Detection Techniques", Human Mutation, 1997, 370-373, vol. 9, No. 4, Wiley-Liss, New York.

Laurent-Puig, et al., "APC Gene: Database of Germline and Somatic Mutations in Human Tumors and Cell Lines", Nucleic Acid Research, 1998, 269-270, vol. 26, No. 1, Oxford University Press, Surrey.

Kirchgesser, et al., "Optimized Non-Radioactive Protein Truncation Test for Mutation Analysis of the *Adenomatous Polyposis Coli* (APC) Gene", Clinical Chemistry and Laboratory Medicine, 1998, 567-570, vol. 36, No. 8, Walter de Gruyter, Berlin.

Vogelstein, et al., "Digital PCR", Proceedings of the National Academy of Sciences of USA, Aug. 1999, 9236-9241, vol. 96.

Dunnen, et al., "The Protein Truncation Test: A Review", Human Mutation, 1999, 95-102, vol. 14, No. 2, Wiley-Liss, New York.

Ahlquist, et al., "Colorectal Cancer Screening by Dectection of Altered Human DNA in Stool: Feasibility of a Multitarget Assay Panel", Gastroenterology, Nov. 2000, 1219-1227, vol. 119, Elsevier, PA.

Human Gene Mutation Database online, "*Adenomatous polyposis coli*" (2005).

Houlston RS, "What we could do now: molecular pathology of colorectal cancer", J. Clin. Pathol.: Mol. Pathol., vol. 54, pp. 206-214 (2001).

Narayan, S. et al., "Role of APC and DNA mismatch repair genes in the development of colorectal cancers", Mol. Cancer, vol. 2, pp. 41-56 (2003).

European Search Reported mailed Sep. 22, 2010 in EP Application No. 10150793.

Romey, Marie-Catherine, et al. "Transcript analysis of CFTR frameshift mutations in lymphocytes using the reverse transcription-polymerase chain reaction technique and the protein truncation test," Human Genetics vol. 98, No. 3, 328-332 (1996).

Zhou, Wei, et al. "Counting alleles reveals a connection between chromosome 18q loss and vascular invasion," Nature Biotechnology 19, 78-81 (2001).

\* cited by examiner

Increasing Signal:Noise by Immuno-selection

A

Mixture of Proteins

B

▲ = 6-His

▬ = FLAG

⊥ = Anti-FLAG antibody

⋏ = Nickel Beads

Wash and keep flow through

SEQUENCE LISTING

```
<160> NUMBER OF SEQ ID NOS: 27

<210> SEQ ID NO 1
<211> LENGTH: 23
<212> TYPE: DNA
<213> ORGANISM: Homo sapiens

<400> SEQUENCE: 1
ggtaattttg aagcagtctg ggc                                              23

<210> SEQ ID NO 2
<211> LENGTH: 23
<212> TYPE: DNA
<213> ORGANISM: Homo sapiens

<400> SEQUENCE: 2
acgtcatgtg gatcagccta ttg                                              23

<210> SEQ ID NO 3
<211> LENGTH: 89
<212> TYPE: DNA
<213> ORGANISM: Homo sapiens

<400> SEQUENCE: 3
ggatcctaat acgactcact atagggagac caccatgatg atgatgatga tgatgatgat      60
gatgatgtct ggacaaagca gtaaaaccg                                        89
```

```
<210> SEQ ID NO 4
<211> LENGTH: 33
<212> TYPE: DNA
<213> ORGANISM: Homo sapiens

<400> SEQUENCE: 4 tttttttttaa cgtgatgact ttgttggcat ggc                              33

<210> SEQ ID NO 5
<211> LENGTH: 9
<212> TYPE: DNA
<213> ORGANISM: Homo sapiens

<400> SEQUENCE: 5 aaagaaaga                                                           9

<210> SEQ ID NO 6
<211> LENGTH: 10
<212> TYPE: DNA
<213> ORGANISM: Homo sapiens

<400> SEQUENCE: 6
gaaaaaaact                                                         10

<210> SEQ ID NO 7
<211> LENGTH: 10
<212> TYPE: DNA
<213> ORGANISM: Homo sapiens

<400> SEQUENCE: 7
cttgatagtt                                                         10

<210> SEQ ID NO 8
<211> LENGTH: 11
<212> TYPE: DNA
<213> ORGANISM: Homo sapiens

<400> SEQUENCE: 8
tgcttcctgt g                                                       11

<210> SEQ ID NO 9
<211> LENGTH: 11
<212> TYPE: DNA
<213> ORGANISM: Homo sapiens

<400> SEQUENCE: 9
tgcttactgt g                                                       11

<210> SEQ ID NO 10
<211> LENGTH: 13
<212> TYPE: DNA
<213> ORGANISM: Homo sapiens

<400> SEQUENCE: 10
atcttttctt tta                                                     13

<210> SEQ ID NO 11
<211> LENGTH: 11
<212> TYPE: DNA
<213> ORGANISM: Homo sapiens

<400> SEQUENCE: 11
cacaggaagc a                                                       11
```

```
<210> SEQ ID NO 12
<211> LENGTH: 11
<212> TYPE: DNA
<213> ORGANISM: Homo sapiens

<400> SEQUENCE: 12
gtgtccttcg t                                                          11

<210> SEQ ID NO 13
<211> LENGTH: 4
<212> TYPE: PRT
<213> ORGANISM: Homo sapiens

<400> SEQUENCE: 13

Thr Gln Glu Ala
 1

<210> SEQ ID NO 14
<211> LENGTH: 11
<212> TYPE: DNA
<213> ORGANISM: Homo sapiens

<400> SEQUENCE: 14
cacagtaagc a                                                          11

<210> SEQ ID NO 15
<211> LENGTH: 11
<212> TYPE: DNA
<213> ORGANISM: Homo sapiens

<400> SEQUENCE: 15
gtgtcattcg t                                                          11

<210> SEQ ID NO 16
<211> LENGTH: 17
<212> TYPE: DNA
<213> ORGANISM: Homo sapiens

<400> SEQUENCE: 16
cagaaaaaac tattgat                                                    17

<210> SEQ ID NO 17
<211> LENGTH: 17
<212> TYPE: DNA
<213> ORGANISM: Homo sapiens

<400> SEQUENCE: 17
gtcttttttg ataacta                                                    17

<210> SEQ ID NO 18
<211> LENGTH: 6
<212> TYPE: PRT
<213> ORGANISM: Homo sapiens

<400> SEQUENCE: 18

Ala Glu Lys Thr Ile Asp
 1               5

<210> SEQ ID NO 19
<211> LENGTH: 18
<212> TYPE: DNA
<213> ORGANISM: Homo sapiens

<400> SEQUENCE: 19
cagaaaaaaa ctattgat                                                   18
```

```
<210> SEQ ID NO 20
<211> LENGTH: 18
<212> TYPE: DNA
<213> ORGANISM: Homo sapiens

<400> SEQUENCE: 20 gtctttttt gataacta                                                    18

<210> SEQ ID NO 21
<211> LENGTH: 5
<212> TYPE: PRT
<213> ORGANISM: Homo sapiens

<400> SEQUENCE: 21

Ala Glu Lys Asn Tyr
 1               5

<210> SEQ ID NO 22
<211> LENGTH: 23
<212> TYPE: DNA
<213> ORGANISM: Homo sapiens

<400> SEQUENCE: 22
taaaagaaaa gattggaact agg                                             23

<210> SEQ ID NO 23
<211> LENGTH: 23
<212> TYPE: DNA
<213> ORGANISM: Homo sapiens

<400> SEQUENCE: 23
attttctttt ctaaccttga tcc                                             23

<210> SEQ ID NO 24
<211> LENGTH: 9
<212> TYPE: PRT
<213> ORGANISM: Homo sapiens

<400> SEQUENCE: 24

Ile Lys Glu Lys Ile Gly Thr Tyr Arg
 1               5

<210> SEQ ID NO 25
<211> LENGTH: 18
<212> TYPE: DNA
<213> ORGANISM: Homo sapiens

<400> SEQUENCE: 25
taaaagattg gaactagg                                                   18

<210> SEQ ID NO 26
<211> LENGTH: 18
<212> TYPE: DNA
<213> ORGANISM: Homo sapiens

<400> SEQUENCE: 26
attttctaac cttgatcc                                                   18

<210> SEQ ID NO 27
<211> LENGTH: 5
<212> TYPE: PRT
<213> ORGANISM: Homo sapiens

<400> SEQUENCE: 27
```

```
Ile Lys Asn Trp Asn
1               5
```

US 7,910,300 B2

DISEASE DETECTION BY PROTEIN TRUNCATION ASSAYS

This application claims the benefit of provisional application Ser. No. 60/336,177 filed Dec. 6, 2001.

This invention was made using funds from the U.S. government. The government retains certain rights in the invention according to the terms of grants CA57345 and CA62924.

TECHNICAL FIELD OF THE INVENTION

This invention is related to the field of disease diagnosis and prognosis. In particular it relates to the detection of mutations in genes which are associated with a disease state or with predisposition to disease.

BACKGROUND OF THE INVENTION

A revolution in fundamental knowledge about the molecular basis of human cancer has occurred in the last fifteen years. One major challenge for the future is to apply this ever-expanding knowledge to the management of patients. Most efforts in this regard have been devoted to therapeutic strategies, and exciting advances have occasionally been made, such as those recently reported for breast cancer[1] and CML[2]. Much less work has been devoted to diagnostic applications, even though early detection through enhanced diagnosis is widely believed to be a very effective strategy to reduce cancer mortality. Deaths from cervical cancers, for example, have decreased dramatically since the advent of routine Pap smears despite the fact that treatment for cervical cancers has not improved dramatically.

Several established strategies for the early detection of colorectal tumors have been devised. Colonoscopy, sigmoidoscopy, and barium enemas provide highly specific and sensitive tests for neoplasia[3-6], but are invasive and are limited by available expertise and patient compliance[7,8]. Testing for occult blood in the stool (FOB) has in some studies been shown to reduce incidence, morbidity and mortality from colorectal cancer[9-13]. These FOB tests are non-invasive and extremely useful, but are not completely sensitive or specific for neoplasia[14-17]. Furthermore, some FOB tests require patients to change their dietary habits prior to testing or require multiple tests, potentially reducing compliance[7,18,19]. There is thus a pressing need to develop new diagnostic tests that overcome these obstacles.

One of the most promising classes of new diagnostic markers comprises mutations in oncogenes and tumor suppressor genes[20]. As these mutations are directly responsible for neoplastic growth, they have clear conceptual advantages over indirect markers for neoplasia such as fecal occult blood. Furthermore, because these mutations only occur in a clonal fashion in neoplastic cells, they theoretically have very high specificity. Several groups have reported that mutations in cancer-related genes can be detected in the stool of colorectal cancer patients[21-35]. However, the sensitivities and specificities achieved have been limited either by technical impediments or low frequencies of detectable mutations in any specific gene. To increase sensitivity, investigators have recently combined tests for mutations in several different genes or combined tests for genetic alterations with other DNA-based tests that are independent of mutation[32-34]. There is a continuing need in the art for diagnostic methods for detection of early stages of cancer and other diseases.

SUMMARY OF THE INVENTION

According to one embodiment of the invention a method is provided of detecting tumors. A test sample of APC alleles isolated from a patient is divided to form a plurality of aliquots of APC alleles. The APC alleles in said plurality of aliquots are amplified to form amplified APC alleles. The proteins are transcribed and translated in vitro using the amplified APC alleles as transcription templates. Size or composition of the proteins is determined. Proteins which differ in size or composition from the protein produced by a wild-type APC allele indicate a mutation in an amplified APC allele which indicates a tumor in the patient.

According to another embodiment of the invention a method is provided for detecting a disease associated with a mutation in a gene. A test sample of alleles of the gene isolated from a patient is divided to form a plurality of aliquots of alleles of the gene. The alleles in the plurality of aliquots are amplified to form amplified alleles. The proteins are transcribed and translated in vitro using said amplified alleles as transcription templates. The size or composition of the proteins is determined. Proteins which differ in size or composition from the protein produced by a wild-type allele of the gene indicate a mutation in an amplified allele of the gene which indicates the disease in the patient. The present invention thus provides the art with diagnostic methods for detection of early stages of cancer and for detecting other diseases

BRIEF DESCRIPTION OF THE DRAWINGS

FIG. 5A: The protein of interest is labeled specifically at the N and C termini with distinct epitopes. This allows the separation of full length protein (wild-type) from truncated ones. FIG. 5B: The signal to noise ratio can be dramatically improved by eliminating the full length proteins from the mixture as depicted by the immunoprecipitation with the FLAG antibody. The remaining truncated products can be directly analyzed or further purified by a second immunoselection.

FIGS. 6A and 6B are pictures of the same gel with a greater exposure in FIG. 6B. An SDS-PAGE gel was used to separate fluorescently labeled proteins which had undergone immuno-selection of APC proteins containing N-term-6-His and C-term-FLAG. Lanes 1-3 contain the full length protein captured with FLAG antibody. Lanes 1-3 contain varying amounts of mutant (truncation-producing) template relative to the full length: lane 1=1/24, lane 2=1/12 and lane 3=1/6. Lanes 4-6 contain the truncated product which was eluted from nickel agarose beads.

DETAILED DESCRIPTION

Figure 1:
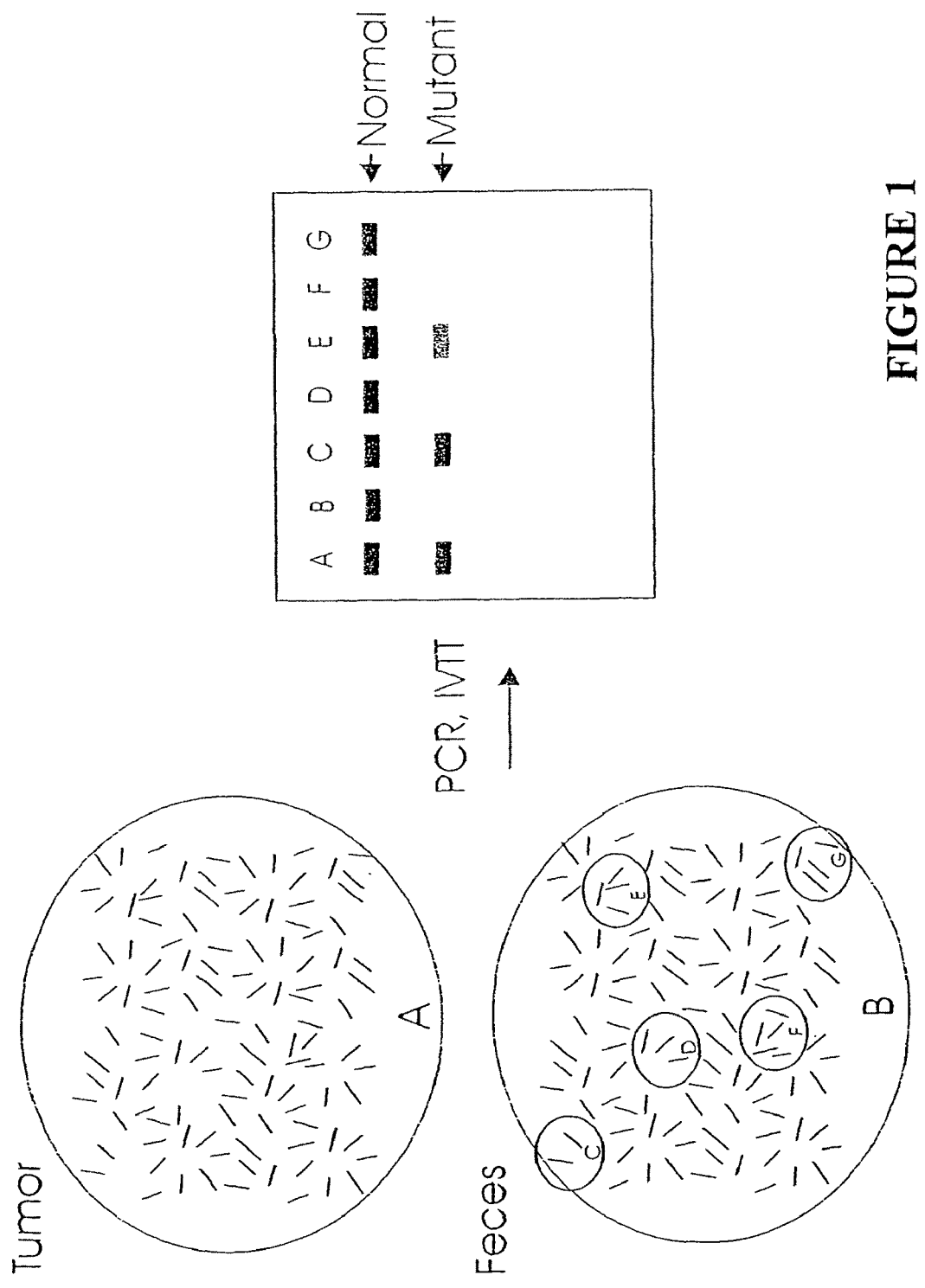
FIG. 1. Digital Protein Truncation Test. Dig-PT relies on two basic principles: (1) the amplification of a small number of APC gene templates in each PCR, and (2) the detection of truncated polypeptides generated by in vitro transcription and translation (IVTT) of the PCR products. The small lines in the left panel represent single stranded APC templates present in a DNA population, with solid and dotted lines indicating wild-type and mutant APC gene copies, respectively. Two situations are illustrated in circles A and B. In circle A, the mutant APC genes represent a large fraction of the total APC genes, as would be found in a tumor. Analysis of the whole population of molecules by PCR/IVTT readily reveals the mutant product, which is equivalent in intensity to the normal APC product (lane A in the gel on the right). In Circle B, the mutant APC genes represent only a small fraction of the total APC genes, as would be found in the feces of a patient with colorectal cancer. Analysis of the whole population of molecules by PCR/IVTT does not reveal the mutant product, as it is present in too small a proportion of the molecules to create a detectable signal in the assay (lane B on the right). To reduce the complexity and thereby increase the mutant:wild-type ratio, ~4 molecules were sampled in each well; the circles labeled C to G within circle B surround the APC gene copies that were amplified in individual wells. Lanes D, F, and G represent wells with no mutant products; lane C represents a well in which one of the two APC templates was mutant; lane E represents a well in which one of four templates was mutant. The APC gene copies per well vary stochastically according to a Poisson distribution.

It is a finding of the present invention that diseases can be detected at an early stage using techniques which increase the signal to noise ratio. Means for increasing the signal to noise ratio include elimination of noise (other DNA) by diluting or dividing a sample to an extent that the signal represents a larger fraction of the total than initially. Such techniques permit the use of highly specific tests, such as protein truncation tests, which may lack the ability to detect highly dilute signals.

Protein truncation tests are useful for detecting mutations that result in stop codons, e.g., as a result of nonsense substitutions or out-of frame deletions or insertions. Such tests are the standard method for genetic diagnosis of familial adenomatous polyposis (FAP). These techniques are described in Powell S M, Petersen G M, Krush A J, et al. Molecular diagnosis of familial adenomatous polyposis, N Engl J Med 1993; 329:1982-7, and van der Luijt R, Khan P M, Vasen H, et al. Rapid detection of translation-terminating mutations at the adenomatous polyposis coli (APC) gene by direct protein truncation test, Genomics 1994; 20:1-4, which are expressly incorporated herein. Briefly, analyte DNA markers are transcribed and translated in vitro and the size or composition of the products is determined. Typically the products are analyzed by gel electrophoresis, which can detect aberrant migration as a change in size or amino acid composition, but other methods can be used, including but not limited to gel chromatography. Protein products can be analyzed using mass spectroscopy, for example. Any technique for determining properties of protein can be used, including immunological and sequencing techniques.

Templates can be obtained using any technique known in the art. Hybridization can be used to enrich for desired templates, using such reagents as beads, magnetic beads, chromatographic column packing matrix, and the like, which have attached sequence-specific oligonucleotides. The oligonucleotides will bind templates of the desired gene which is to be analyzed. Bound templates can be eluted using any technique which separates duplex DNA into single strands, such as heating above the $T_M$.

Desirably a small number of template molecules for a DNA marker are analyzed in multiple aliquots. The aliquots can be made by dividing up a single sample or by diluting a sample. Preferably each aliquot will contain less than 20 templates. More preferably each aliquot will contain less than 10, less than 5, or less than 2 templates. At least some of the aliquots should contain at least 1 template, at least 5 templates or at least 10 templates. Using such small number of template molecules in each aliquot permits detection of mutations in templates which occur in less than 15% of template molecules.

Amplification of templates can be accomplished by any linear or exponential technique, including but not limited to polymerase chain reaction and rolling circle amplification. All or a portion of the desired analyte gene can be amplified. Preferably the mutation spectrum of the analyte gene will be known and the amplified portion will contain the majority of the mutations which occur in the population being tested. For example in the APC gene, about 65% of sporadic tumors harbor APC mutations in exon 15, between codons 1210 to 1581.

Transcription and translation can be performed using any particular techniques known in the art. Products can be labeled, for example, using radiolabeled or fluorescently labeled amino acids and can be detected using autoradiography or scintillation counting. Products can also be analyzed and/or enriched using antibodies which recognize the products, including products which contain short oligopeptide tags. Antibodies to N- and C-terminal epitopes, whether naturally occurring epitopes or introduced during amplification, can be used to immunoselect rare products or immunodeplete abundant products. The antibodies can be used in conjunction with solid supports such as beads, magnetic beads, filters, microtiter dishes, column packing materials, etc. N-terminal and C-terminal epitopes may be, but need not be the epitopes formed by the most terminal amino acids. Epitopes from these general regions, i.e., within the terminal 1/10, 1/8, 1/5, 1/4, or 1/3 of a protein may be used. Any detection and sizing methods known in the art can be used. Optionally, amplified products can be sequenced to ascertain the identity of a mutation which causes a truncated protein product.

Any means can be used for isolation of a DNA from a sample of a human or other test animal. Stool samples can be treated, for example, as disclosed in U.S. Pat. No. 6,177,251 or 5,910,407. Other samples which can be used as sources of DNA include tears, saliva, urine, biopsy samples, tumor margins, serum, blood, plasma, endometrial washings, nipple aspirates, semen, and bronchoalveolar lavage. Other body fluids and exudates can be used as is appropriate for the particular disease.

When a disease is referred to in the present application it includes a finding of a predisposition to the disease. For example, an APC mutation can be inherited and cause a predisposition to develop colorectal and other cancers. APC mutations can also occur somatically in sporadic tumors. Mutations in APC indicate either the disease state or the predisposition Other diseases which can be detected using the present method include but are not limited to hereditary non-polyposis colon cancer, cystic fibrosis, von Hippel Landau disease, and neurofibromatosis.

The above disclosure generally describes the present invention. A more complete understanding can be obtained by reference to the following specific examples which are provided herein for purposes of illustration only, and are not intended to limit the scope of the invention.

Example 1

Methods Employed in the Subsequent Examples

Patients and Samples

A total of 68 stool samples were derived from a sequential collection of 315 patients evaluated at M.D. Anderson Cancer Center or surrounding hospitals between 1997 and 2000 for suspected colorectal neoplasia. Of these patients, 77 had cancer, including 30 with Dukes' B2 (T3N0M0) disease, five with in situ lesions, six with Duke's A, five with Duke's B1, 20 with Duke's C, nine with Duke's D, and two of unknown/other classes. We chose to focus on the Duke's B2 cases because these were the most common class and because the great majority of B2 cancers should be surgically curable, maximizing the potential impact of diagnostic detection through analysis of stool. We excluded two of these 30 cases because of other colonic lesions found at colonoscopy or surgery, potentially complicating analysis. To control for the 28 cancer patients, 28 control patients from the same cohort were selected randomly from among the 55 patients who proved to be tumor-free upon colonoscopy. The reasons for performing colonoscopy in these controls included positive FOBT, rectal bleeding, or personal or family history of colorectal neoplasia (Table 2).

From among this same 315 patient cohort, 12 patients were identified who had single adenomas ≧1 cm in diameter. Stools from patients with adenomas of this size were chosen because such adenomas have an 8% chance of progressing to malignancy within ten years after diagnosis, while smaller adenomas have a low risk of progression[44,45]. We additionally examined stool samples from six patients with adenomas ≧1 cm in diameter from the Lahey Clinic. These patients represented all those found to have adenomas of this size among 172 patients referred to the Lahey Clinic for a screening or diagnostic colonoscopy between September, 2000 and June, 2001.

Stool samples were collected prior to colonoscopy from 19 of the 46 patients with neoplasia and prior to surgery in the remainder. All stool samples were collected prior to colonoscopy in the controls. Patients received detailed oral and written instructions for stool collection, which were all obtained prior to beginning laxative treatments to prepare for surgery or colonoscopy. None of the patients had familial adenomatous polyposis or hereditary non-polyposis colon cancer. Verbal or written informed consent was obtained from each patient, documenting their willingness to participate in the laboratory-based study. The work was carried out in accordance with the institutional review boards at The University of Texas M.D. Anderson Cancer Center, The Johns Hopkins Medical Institutions (Baltimore, Md.), the Baylor College of Medicine, St. Luke's Episcopal Hospital (Houston, Tex.), and the Lahey Clinic (Burlington, Mass.).

Purification of DNA

Purification of DNA was performed using modifications of procedures described in Ahlquist et al.[32]. All stool samples were thawed at room temperature and homogenized with an EXACTOR stool shaker (EXACT Laboratories, Maynard, Mass.). After homogenization, a 4-g stool equivalent of each sample was subjected to two centrifugations (2536 g, 5 minutes and 16,500 g, 10 minutes) to remove large and small particulate matter, respectively. Supernatants were incubated with 20 μL RNase (0.5 mg/mL) for 1 hour at 37° C., followed by a precipitation with 1/10 volume 3 mol/L NaOAc and an equal volume of isopropanol. The crude DNA was dissolved in 10 mL of TE (0.01 mol/L Tris [pH7.4] and 0.001 mol/L EDTA). Hybrid capture of APC genes was performed by adding 300 μL of sample to an equal volume of 6 mol/L guanidine Isothiocyanate solution (Invitrogen, Carlsbad, Calif.) containing biotinylated sequence-specific oligonucleotides (20 μmol; Midland Certified Reagent C., Midland, Tex.). After a 12-hour incubation at 25° C., streptavidin-coated magnetic beads were added to the solution, and the tubes incubated for an additional hour at room temperature. The bead/hybrid capture complexes were then washed four times with 1×B+W buffer (1 mol/L NaCl, 0.01 mol/L Tris-HCl [pH7.2], 0.001 mol/L EDTA, and 0.1% Tween 20), and the sequence-specific captured DNA was eluted into 85° C. pre-warmed 40 μL L-TE (1 mmol/L Tris [pH7.4] and 0.1 mol/L EDTA) for 4 minutes. The concentration of amplifiable APC templates in captured DNA was determined by limiting dilution, using primers F1 and R1 for PCR, carried out as described below.

Digital-PT

1. PCR

Each reaction contained 1×PCR Buffer (Invitrogen, Carlsbad, Calif.), 0.2 mM dNTPs, 2 mM MgSO$_4$, 0.9 μM oligonucleotides F1 and R1, and 0.015 U/μl Platinum Taq DNA Polymerase High Fidelity (Invitrogen, Carlsbad, Calif.). A single PCR mix, containing ~580 APC template molecules, was prepared for each stool sample and the mix aliquotted to 144 wells; each well therefore contained ~four APC templates. After an initial denaturation at 94° C. for 2 minutes, amplifications were performed as follows: 3 cycles of: 94° C. for 30 seconds, 67° C. for 30 seconds, 70° C. for 1 minute; 3 cycles of: 94° C. for 30 seconds, 64° C. for 30 seconds, 70° C. for 1 minute; 3 cycles of: 94° C. for 30 seconds, 61° C. for 30 seconds, 70° C. for 1 minute; 50 cycles of: 94° C. for 30 seconds, 58° C. for 30 seconds, 70° C. for 1 minute. One μL of the reaction was added to a 10-μL PCR reaction of the same makeup as the one described above except that primers F2 and R2 were used. Following a 2 minute denaturation step at 94° C., the reaction was cycled for 15 cycles of 94° C. for 30 seconds, 58° C. for 30 seconds, 70° C. for 1 minute. Primer sequences were:

```
                                              (SEQ ID NO: 1)
F1, 5'-GGTAATTTTGAAGCAGTCTGGGC-3';

(SEQ ID NO: 2)
R1, 5'-ACGTCATGTGGATCAGCCTATTG-3';

(SEQ ID NO: 3)
F2: 5'-GGATCCTAATACGACTCACTATAGGGAGACCACCATGATGATGA
TGATGATGATGATGATGATGATGTCTGGACAAAGCAGTAAAACCG-3';
and (SEQ ID NO: 4)
R2: 5'-TTTTTTTTAACGTGATGACTTTGTTGGCATGGC-3'.
```

2. In Vitro Transcription and Translation

In vitro transcription and translation was performed in 5-μL volumes in 96-well polypropylene PCR plates. Reactions consisted of 4-μL TnT T7 Quick for PCR DNA (Promega, Madison, Wis.), 0.25-μL $^{35}$S-Promix (Amersham Pharmacia Biotech, Piscataway, N.J.), 0.25-μL dH$_2$O, 0.5-μL of F2/R2 PCR products. Reactions were covered with mineral oil and incubated at 30° C. for 90 minutes, then diluted with Laemmli sample buffer and denatured at 95° C. for 2 minutes. Proteins were separated on 10-20% Tris-Glycine gradient polyacrylamide gels, then fixed in ethanol and dried prior to autoradiography.

Sequencing Studies

PCR products from wells yielding truncated peptides in the Dig-PT assay were isolated and gel purified using the QIAquick Gel Extraction kit (Qiagen, Valencia, Calif.). The DNA was then cloned using the TOPO Cloning kit (Invitrogen, Carlsbad, Calif.). Single colonies were used for PCR and the products sequenced with dye terminators (Applied Biosystems Prism Cycle Sequencing, v. 3.0). Sequencing reactions were analyzed on an SCE-9610 96-well capillary electrophoresis system (SpectruMedix Corporation, State College, Pa.). In seven cases, DNA was prepared from archived tumors and small regions of the APC amplified and subjected to manual sequence analysis with ThermoSequinase (Amersham Pharmacia, Inc., Piscataway, N.J.) to confirm that the mutations identified in stool were also present in the patient's tumors.

Example 2

Development of Dig-PT Assay

The intent of the current study was to develop a single gene-based test that would facilitate the specific detection of clinically significant but pre-metastatic colorectal tumors. Conceptually, the optimal gene for such studies is APC[36,37]. APC mutations generally initiate colorectal neoplasia and therefore are present in tumors at an earlier stage than any other genetic alteration[38]. Other mutations, like those in p53, are present only in the later stages of colorectal neoplasia[39] or, like those in c-Ki-RAS, may be present in non-neoplastic but hyperproliferative cells[40-42]. Practically, however, detection of mutations in APC present extraordinarily difficult technical challenges. Unlike c-Ki-RAS gene mutations, which have been used for most previous studies because mutations are clustered at two codons, mutations in APC can occur virtually anywhere within the first 1600 codons of the gene[43]. Moreover, the nature of individual mutations (base substitutions, insertions or deletions of diverse length) varies widely among tumors. Though such APC mutations can be detected relatively easily in tumors, where they are present in every neoplastic cell, they are much harder to detect in fecal DNA, where they may be present in less than one in a hundred of the total APC genes present in the sample. Herein we describe an approach that allowed us to detect such mutations in the fecal DNA of cancer patients in a highly precise, specific, and quantitative fashion.

The detection of APC mutations in fecal DNA required us to surmount two major technical hurdles. The first involved purification of DNA templates that were of sufficient size to allow PCR of a substantial region of the APC gene. It has been demonstrated previously that ~65% of sporadic tumors harbor APC mutations between codons 1210 and 1581, representing an expanse of 1113 nucleotides[43]. For our analysis, it was important to be able to amplify this region within a single PCR product rather than in multiple overlapping PCR products. The DNA molecules to be assessed must therefore be considerably larger than 1100 nt. However, stool contains numerous inhibitors of DNA polymerization, and long PCR products, such as those of 1100 bp, are particularly sensitive to such inhibitors. During the developmental stages of this study, we explored numerous methods for stool homogenization, DNA purification, and PCR conditions. The final method, employing affinity capture, resulted in routine amplification of fragments of the required size from the stools of all 56 individuals analyzed. A median of 4.3 and 2.3 APC gene copies/mg stool were found in patients with and without colorectal neoplasia, respectively, with wide variations from patient to patient (Tables 1 & 2).

The second technical hurdle involved the identification of mutations within these PCR products. It has previously been shown that virtually all APC mutations result in stop codons as a result of nonsense substitutions or small out-of-frame deletions or insertions[43]. APC mutations can therefore be identified through in vitro transcription and translation of suitably engineered PCR products[46,47]. This "in vitro synthesized protein (IVSP)" or "protein truncation (PT)" test is the standard method for genetic diagnosis of familial adenomatous polyposis (FAP). However, this method could not be used to evaluate fecal DNA samples because of the high preponderance of wild-type sequences over mutated sequences in such samples. In particular, the sensitivity of the conventional method was limited to mutations that were present in more than 15% of template molecules while mutant APC genes were expected to be present in fecal DNA at much lower frequency. We therefore developed a modification of this method, called Digital Protein Truncation (Dig-PT), that considerably increased its sensitivity. In brief, a small number of template molecules was included in each reaction and the protein products of each reaction separated through polyacrylamide gel electrophoresis (FIG. 1). In this way we could analyze as many gene copies as desired from each sample. In the current study, we chose to assess 144 reactions each containing ~4 APC gene copies. To increase the specificity of Dig-PT and to control for polymerase-generated errors, the test was scored positive for mutation only when the same size truncated protein product was identified at least twice among the ~576 APC gene copies analyzed.

Example 3

Analysis of Cancer Patients and Controls

Figure 2:
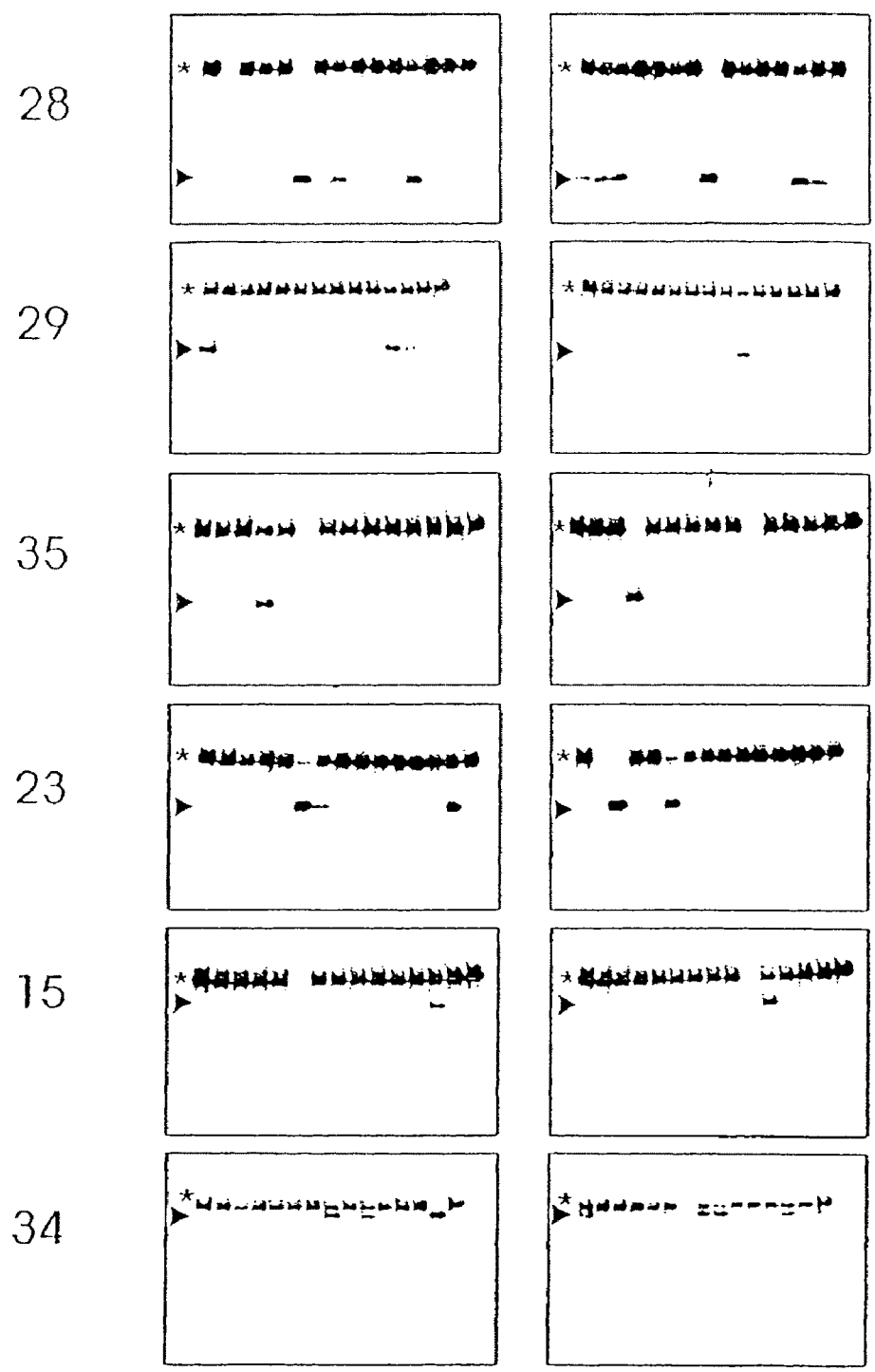
FIG. 2. Examples of Dig-PT results. Dig-PT analyses of six patients (ID #28, 29, 35, 23, 15 and 34) with truncating mutations in APC are displayed. The wild-type protein product is 43 kDa (asterisk). The transcription-translation products from 30 individual reactions are shown in each case, and the abnormal polypeptides are indicated by arrowheads. Because of the Poisson distribution of template molecules, an occasional lane will contain no templates and will be blank (e.g., lane 2 in patient #28).

Dig-PT was used to analyze stool samples from the 74 patients described in Methods. Of the 46 patients with neoplasia, mutations were identified in 26 (57%, CI 41% to 71%). Representative positive Dig-PT assays are shown in FIG. 2. In FIG. 2, for example, it is clear that several independent PCR products from stool #5 generated a truncated polypeptide of 12 kDa in addition to the normal protein of 43 kDa in size. Different truncated polypeptides were identified in other patients (FIG. 2). No mutations were identified in the Dig-PT assay in the 28 control individuals without neoplastic disease (0%, CI 0 to 12%). The difference between patients with and without neoplastic disease was highly significant (2-sided p<0.001, Fishers exact test). Positive Dig-PT results were obtained in patients with both cancer (61% of 28) and pre-malignant adenomas (50% of 18). Additionally, positive Dig-PT results were observed in 56% of 36 patients with neoplasms distal to the splenic flexure and in 60% of ten patients with more proximal lesions. There was also no appreciable difference in our ability to detect mutations in stools collected prior to colonoscopy (53% of 19 cases) vs. those collected after colonoscopy but prior to surgery (59% of 27 cases). In those patients scoring positive, the fraction of altered APC genes ranged from 0.4% to 14% of the total APC genes in the stool sample (Table 1).

Example 4

Confirmation of Mutations

Figure 3:
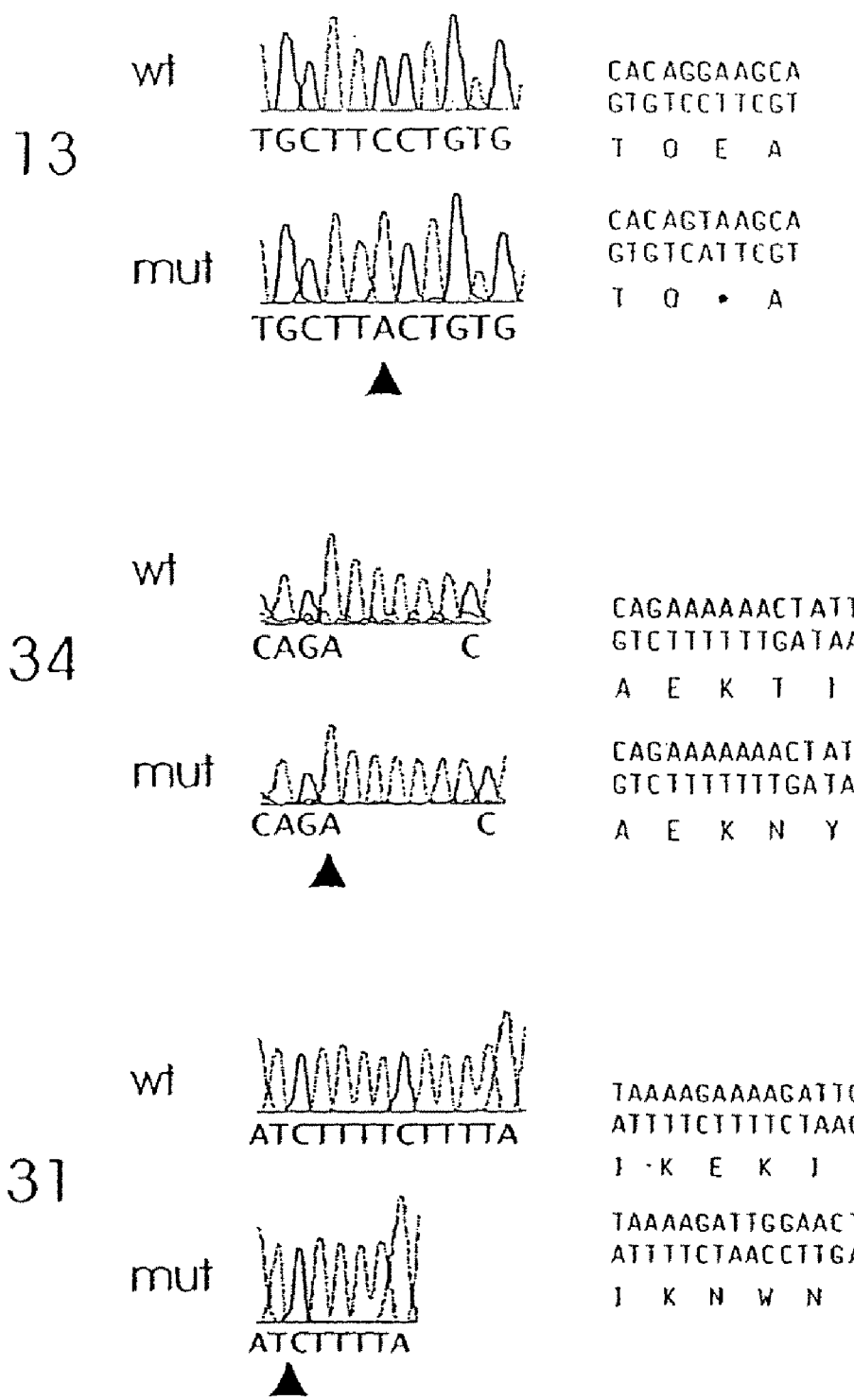
FIG. 3. Identification of the mutations producing truncated polypeptides in Dig-PT. PCR products that generated abnormal polypeptides in Dig-PT were used for sequence analyses as described in the Methods. In each case, primers were chosen based on the position of the mutation expected from the Dig-PT results. The top chromatogram in each case represents the wild-type (wt) sequence while the bottom chromatogram depicts the mutant (mut) sequence (black arrowheads mark site of genetic alteration). Examples of a base substitution (Patient #13), on bp insertion (Patient #34) and a five bp deletion (Patient #31) are illustrated. All mutations resulted in stop codons (black circles) immediately downstream of the mutations, as indicated on the right.
Figure 4:
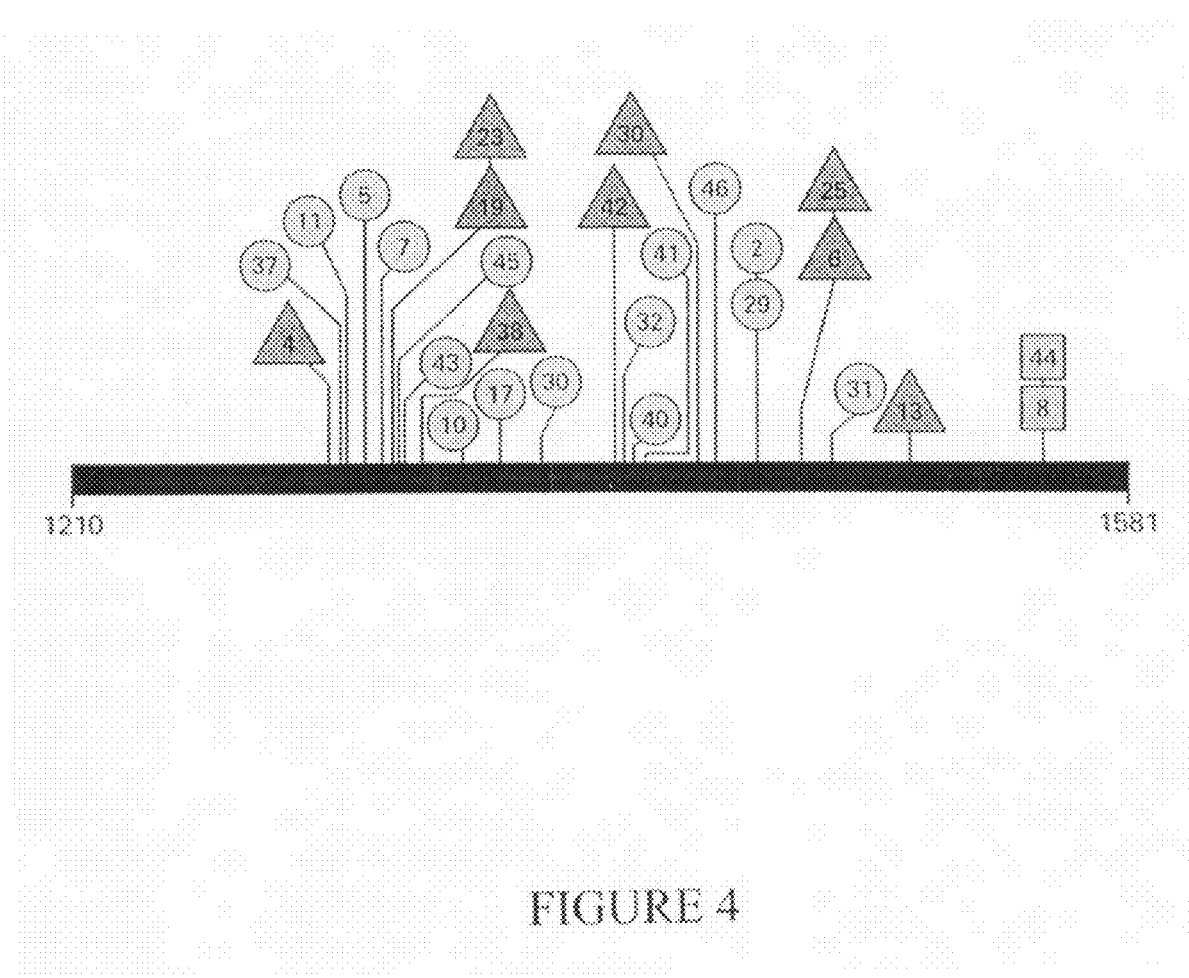
FIG. 4. APC mutation spectrum in fecal DNA. The black bar depicts the APC region queried. A total of 21 different mutations were identified among the 23 patients with positive Digital-PT tests. Mutations occurred in the form of deletions (triangles), insertions (squares) and base substitutions (circles). The numbers within the symbols refer to patient ID # (Table 1).

The Dig-PT assay provided evidence for mutations that were predicted to truncate the protein at specific positions within the gene. To confirm that the abnormal polypeptides observed in this assay represented APC mutations, and to determine the nature of these mutations, we determined the sequence of corresponding PCR products. The PCR products from two wells whose transcription/translation products produced truncated proteins of identical size were purified and cloned from each patient scoring positively in the Dig-PT assay. These cloned PCR products were then subjected to automated sequencing. In each of the 26 cases, we observed a mutation that was predicted to result in a truncated polypeptide of exactly the size observed in the Dig-PT assay (examples shown in FIG. 3). The spectrum of mutations was broad, with 27 different mutations identified in the 26 samples (FIG. 4). Sixteen (59%) of these mutations were nucleotide substitutions resulting in nonsense mutations, two (7.4%) were small insertions, and nine (33%) were small deletions (Table 1). The frequency and type of these mutations closely resembled those described previously in sporadic colorectal tumors[43]. The insertions and deletions resulted in frameshifts producing stop codons 2 to 49 bp downstream from the sites of mutation.

Example 5

Immuno-Selection of Truncated APC Proteins

As described above, one way of improving the signal-to-noise ratio is by way of a controlled dilution of the DNA sample. It is also possible to improve the signal-to-noise ratio at the protein level by subtracting full-length protein from a mixed population of truncated and full-length proteins. The protein can be tagged at the N- and C-termini by the addition of distinct epitopes (e.g., HA, FLAG, 6-His, myc, etc.).

Figure 5:
FIG. 5. Schematic of Immuno-selection in stool.
Figure 6:
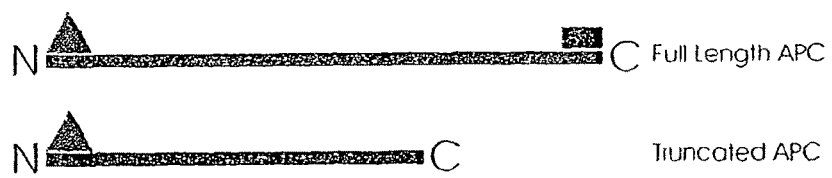
FIG. 6. Immuno-selection of truncated APC proteins with fluorescently labeled amino-acids.
Figure 6:
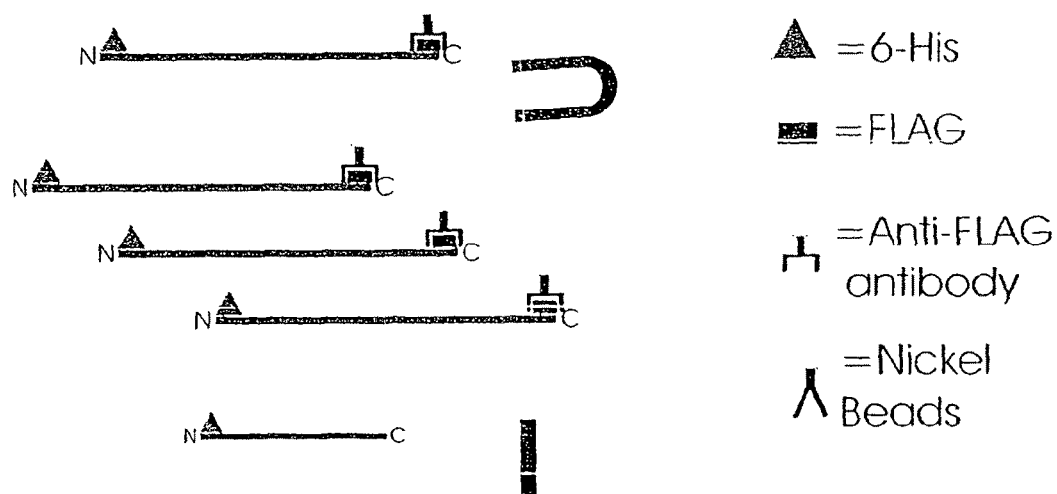
Figure 6:

For example, using the same PCR primers as described above, one can add the 6-His sequence to the F2 primer and the FLAG sequence to the R2 primer. Following translation of the PCR products, "full-length" APC protein product will contain an N terminal 6-His epitope and a FLAG C-terminal epitope. DNA molecules with a truncating mutation will yield truncated proteins which contain only the N-terminal FLAG epitope. The protein mixture can be immunodepleted by incubation with FLAG-agarose beads. (Other solid supports can be used, e.g., magnetic beads, as depicted in the accompanying figure.) The "full-length" proteins will be bound by the beads while the truncated ones will remain in solution. The solution can be analyzed directly or concentrated, e.g., by immunoprecipitating the truncated products with beads containing antibodies to an N-terminal epitope (6-His in FIG. 5). Results of such an experiment are shown in FIGS. 6A and 6B and described in the Brief Description of the Drawings.

Example 6

Discussion

The results described above show that PCR-amplifiable DNA fragments>1100 bp in size could be purified from the stools of all patients analyzed, whether or not they had colorectal neoplasia. The keys to this purification involved affinity purification of APC genes through hybrid capture rather than the physicochemical methods that are conventionally used to purify DNA. Equally important for the success of the amplification was the development of highly efficient methods for producing relatively long PCR products in the presence of inhibitors. The number of DNA molecules in stool samples varied widely, consistent with the large variation of fecal content and volume expected from a diverse American population (Tables 1 & 2). The bulk of DNA in the stool is derived from sloughed normal cells whose number undoubtedly reflects the vagaries of diet and bowel habits. Though intestinal epithelial cells normally turn over at a high rate, most of their DNA appears to be reabsorbed through phagocytosis rather than shed into the stool[48].

In addition to quantifying the number of total APC alleles present in stool, our approach allowed us to determine the fraction of mutant APC molecules present in the same samples. This ranged from 0.4% to 14% in our patients. This variation had little correlation with the size of the tumors, their site, or their malignancy (adenoma vs. carcinoma), but instead was likely determined by the "contaminating" DNA from non-neoplastic cells present in the stool by virtue of the processes described above. Knowledge gained from the current study about the actual fraction of mutant DNA molecules present in stool should prove important to the design of future studies in this area. For example, our results indicate that any technique to assess mutant DNA molecules in fecal DNA must have the capacity to distinguish one mutant molecule from at least 250 wild type molecules if comparable sensitivity is to be achieved.

Another advantage of the approach described here is that only a single PCR product, encompassing APC codons 1210 to 1581 was used for analysis. Prior studies generally employed multiple PCR products from the same gene or from several genes to increase sensitivity. Even with such multiple tests, past studies have not documented sensitivities as high as those described here in patients with equivalent disease status. In particular, our study is the first to focus on relatively early stage lesions. All of the patients we analyzed had either pre-malignant adenomas or pre-metastatic carcinomas. Because of the high potential for cure through surgical or endoscopic removal of these lesions, their detection through non-invasive methods like Dig-PT offers outstanding opportunities for reducing morbidity and mortality in the future.

An important component of our study was the high specificity observed: no APC alterations were identified in any of the 28 controls without neoplasia. Of the published studies on fecal DNA mutations[21-35], few employed more than three stool samples from normal individuals as controls. In one such study, c-Ki-Ras mutations were observed in 7% of the controls[32]. Aberrant crypt foci and small hyperplastic polyps, which occur relatively frequently in normal individuals but are thought not to be precursors to cancer, often contain c-Ki-Ras gene mutations but do not harbor APC mutations[40-42], further emphasizing the value of APC for stool-based testing.

The necessity for an APC-based technique that could reveal multiple different mutations was clear from the mutation spectrum shown in FIG. 4. Only four mutations were found in more than one patient, and the type and location of the detected mutations varied considerably. These data are consistent with the mutations previously found in sporadic colorectal tumors[43]. The fraction of patients positive with the Dig-PT assay (57%) was close to the theoretical fraction of patients expected to be positive from these previous studies (65%). Though tumor material suitable for mutational analyses was not available for most patients, we were able to identify APC mutations in seven primary colorectal cancers, and in each case, the mutation was identical to that found in the stool (examples in FIG. 3).

In summary, it is clearly possible to detect APC mutations in fecal DNA in a substantial fraction of patients with potentially curable colorectal tumors. Our analyses clearly showed that that it was feasible to detect fecal APC mutations in patients whose tumors were pre-malignant or located in the proximal colon (Table 1). It was of interest that five of the control patients in our study had a positive FOBT as the reason for colonoscopy, while in another six, the reason was rectal bleeding, precluding FOBT (Table 2). This result supports the potential value of a more specific genetically-based test for analysis of feces. As Dig-PT screening is based on the identification of abnormal proteins synthesized from mutant genes, the powerful new tools being developed for proteomics should be directly applicable to this approach in the future, further increasing its power.

TABLE 1

Characteristics of Patients with Neoplasia

| Patient ID # | Age | Sex | Site of Cancer | Stage/Histology | Diameter (cm) | APC gene copies/mg stool | Fraction of Mutant APC genes | Mutation identified (codon, normal sequence -> mutant sequence) |
|---|---|---|---|---|---|---|---|---|
| 1 | 36 | Female | Rectum | B2 (T3N0M0) | 1.3 | 40.6 | NF | N/A |
| 2 | 42 | Female | Rectum | B2 (T3N0M0) | 0.2 | 309.8 | 1.3% | 1319, TCG -> TC |
| 3 | 45 | Male | Rectum | B2 (T3N0M0) | 0.5 | 32.7 | NF | N/A |
| 4 | 46 | Female | Rectum | Tubular Adenoma | 2.5 | 5.0 | NF | N/A |
| 5 | 47 | Male | Rectum | B2 (T3N0M0) | 3.0 | 9.7 | 3.6% | 1367, CAG -> TAG; 1411, AGT -> AG* |
| 6 | 47 | Female | Rectum | B2 (T3N0M0) | NR | 75.6 | 1.3% | 1286, ATA -> TA |
| 7 | 50 | Male | Rectum | B2 (T3N0M0) | 1.6 | 57.4 | NF | N/A |
| 8 | 50 | Male | Rectum | B2 (T3N0M0) | 3.7 | 0.1 | 6.6% | 1309, AAAGAAAAGA -> AAAGA |
| 9 | 50 | Male | Rectum | B2 (T3N0M0) | 0.9 | 18.8 | NF | N/A |
| 10 | 52 | Female | Rectum | Villous Adenoma | 3.0 | 26.6 | 1.1% | 1554, GAAAAAACT -> CAAAAAACT |
| 11 | 52 | Female | Transverse | Tubular Adenoma | 4.5 | 591.4 | 0.5% | 1450, CGA -> TGA |
| 12 | 52 | Female | Ascending | Tubulovillous Adenoma | 2.0 | 3.7 | NF | N/A |
| 13 | 52 | Female | Sigmoid | B2 (T3N0M0) | 3.5 | 21.9 | 5.6% | 1295, GAA -> TAA |
| 14 | 53 | Male | Rectum | B2 (T3N0M0) | 1.4 | 18.7 | 12.8% | 1406, CAG -> TAG |
| 15 | 54 | Male | Descending | Tubular Adenoma | 2.0 | 1.6 | 1.0% | 1489, TTA -> TT |
| 16 | 54 | Male | Rectum | B2 (T3N0M0) | 2.4 | 757.8 | NF | N/A |
| 17 | 57 | Male | Splenic Flexure | B2 (T3N0M0) | 6.7 | 6.4 | NF | N/A |
| 18 | 58 | Male | Sigmoid | Tubular Adenoma | 1.0 | 1.4 | 1.2% | 1463, GAG -> G |
| 19 | 60 | Male | Rectum | B2 (T3N0M0) | 4.3 | 0.4 | 2.0% | 1317, GAA -> TAA |
| 20 | 61 | Female | Rectum | Villous Adenoma | 4.5 | 0.2 | NF | N/A |
| 21 | 61 | Female | Rectum | B2 (T3N0M0) | NR | 0.1 | NF | N/A |
| 22 | 62 | Female | Rectum | Villous Adenoma | 3.0 | 1.2 | NF | N/A |
| 23 | 62 | Female | Rectum | B2 (T3N0M0) | 0.6 | 6.6 | 2.3% | 1435, AGA -> TGA |
| 24 | 63 | Male | Rectum | B2 (T3N0M0) | 0.8 | 9.4 | NF | N/A |
| 25 | 64 | Male | Rectum | B2 (T3N0M0) | 2.4 | 5.1 | NF | N/A |
| 26 | 64 | Male | Rectum | B2 (T3N0M0) | 1.3 | 800.0 | 0.4% | 1309, GAA -> TAA |
| 27 | 64 | Male | Rectum | B2 (T3N0M0) | 1.7 | 133.4 | 3.1% | 1353, GAA -> TAA |
| 28 | 67 | Female | Rectum | B2 (T3N0M0) | 1.1 | 2.5 | 14.1% | 1303, CAA -> TAA |
| 29 | 67 | Male | Rectum | B2 (T3N0M0) | 2.4 | 300.0 | 1.9% | 1394, CTTGATAGTT -> CTTGAGTT |
| 30 | 68 | Female | Ascending | B2 (T3N0M0) | 1.7 | 0.2 | NF | N/A |
| 31 | 69 | Male | Rectum | B2 (T3N0M0) | 5.0 | 1.5 | 1.2% | 1309, AAAGAAAAGA -> AAAGA |
| 32 | 70 | Female | Ascending | Tubular Adenoma | 1.0 | 1.3 | 1.9% | 1463, GAG -> G |
| 33 | 70 | Male | Sigmoid | B2 (T3N0M0) | 1.7 | 9.0 | 0.5% | 1480, CAG -> TAG |
| 34 | 70 | Male | Rectum | B2 (T3N0M0) | 1.6 | 1.5 | 5.8% | 1554, GAAAAAACT -> GAAAAAAACT |
| 35 | 73 | Female | Ascending | Tubulovillous Adenoma | 1.0 | 0.2 | 1.8% | 1412, GGA -> TGA |
| 36 | 74 | Female | Sigmoid | Tubulovillous Adenoma | 3.0 | 1.4 | NF | N/A |
| 37 | 75 | Male | Rectum | B2 (T3N0M0) | NR | 59.2 | 0.9% | 1315, TCA -> TAA |
| 38 | 76 | Male | Sigmoid | B2 (T3N0M0) | 1.3 | 2.5 | NF | N/A |
| 39 | 76 | Male | Rectum | B2 (T3N0M0) | 1.4 | 3.5 | 1.6% | 1408, GAA -> TAA |
| 40 | 78 | Male | Hepatic Flexure | Tubulovillous Adenoma | 2.5 | 5.8 | NF | N/A |

NR = Diameter not recorded
NF = Mutation not found
N/A = Not applicable
*= Two different mutations identified by Dig-PT and confirmed by sequencing

TABLE 2

Characteristics of Control Patients

| Patient ID # | Age | Sex | Reason for Colonoscopy | APC gene copies/mg stool |
|---|---|---|---|---|
| C1 | 26 | Male | Abdominal pain, Rectal Bleeding | 40.1 |
| C2 | 27 | Female | FOBT Positive | 3.9 |
| C3 | 35 | Male | Rectal Bleeding | 6.1 |
| C4 | 36 | Female | Low abdominal pain | 0.3 |
| C5 | 36 | Female | Family History of Attenuated polyposis-questionable | 2.3 |
| C6 | 41 | Female | FOBT Positive | 1.8 |
| C7 | 42 | Male | Family History of Colorectal | 7.4 |

TABLE 2-continued

Characteristics of Control Patients

| Patient ID # | Age | Sex | Reason for Colonoscopy | APC gene copies/mg stool |
|---|---|---|---|---|
| C8 | 44 | Female | Rectal Bleeding | 2.3 |
| C9 | 44 | Female | Family History of Colorectal Cancer | 17.4 |
| C10 | 47 | Female | FOBT Positive | 1.4 |
| C11 | 50 | Male | Family History of Colorectal Cancer | 2.6 |
| C12 | 53 | Female | Family History of Colorectal Cancer | 3.8 |
| C13 | 53 | Female | Family History of Cotorectal Cancer | 12.3 |
| C14 | 54 | Female | Family History of Colorectal Cancer | 5.9 |
| C15 | 55 | Female | Family History of Polyps | 1.1 |
| C16 | 55 | Female | History of Adenomas/Nonadenomalous Polyps | 11.8 |
| C17 | 56 | Female | Family History of Colorectal Cancer | 2.0 |
| C18 | 56 | Female | Low abdominal pain | 1.0 |
| C19 | 58 | Female | Rectal Bleeding | 35.7 |
| C20 | 61 | Female | FOBT Positive | 0.7 |
| C21 | 62 | Female | FOBT Positive | 2.4 |
| C22 | 62 | Female | Family History of Colorectal Cancer | 0.1 |
| C23 | 66 | Female | Rectal Bleeding | 1.0 |
| C24 | 69 | Female | Family History of Colorectal Cancer | 0.6 |
| C25 | 69 | Male | Screening | 0.3 |
| C26 | 70 | Female | Family History of Colorectal Cancer | 0.5 |
| C27 | 72 | Female | Rectal Bleeding | 4.7 |
| C28 | 73 | Female | Low abdominal pain | 0.4 |

FOBT = Fecal occult blood test

REFERENCES

1. Slamon D J, Leyland-Jones B, Shak S, et al. Use of chemotherapy plus a monoclonal antibody against HER2 for metastatic breast cancer that overexpresses HER2. N Engl J Med 2001; 344:783-92.
2. Druker B J, Talpaz M, Resta D J, et al. Efficacy and safety of a specific inhibitor of the BCR-ABL tyrosine kinase in chronic myeloid leukemia. N Engl J Med 2001; 344:1031-7.
3. Newcomb P A, Norfleet R G, Storer B E, Surawicz T S, Marcus P M. Screening sigmoidoscopy and colorectal cancer mortality. J Natl Cancer Inst 1992; 84:1572-5.
4. Selby J V, Friedman G D, Quesenberry C P, Jr., Weiss N S. A case-control study of screening sigmoidoscopy and mortality from colorectal cancer. N Engl J Med 1992; 326:653-7.
5. Lieberman D A, Weiss D G, Bond J H, Ahnen D J, Garewal H, Chejfec G. Use of colonoscopy to screen asymptomatic adults for colorectal cancer. Veterans Affairs Cooperative Study Group 380. N Engl J Med 2000; 343:162-8.
6. Imperiale T F, Wagner D R, Lin C Y, Larkin G N, Rogge J D, Ransohoff D F. Risk of advanced proximal neoplasms in asymptomatic adults according to the distal colorectal findings. N Engl J Med 2000; 343:169-74.
7. Trends in Screening for Colorectal Cancer-United States, 1997 and 1999. JAMA 2001; 285:1570-1571.
8. Scotiniotis I, Lewis J D, Strom B L. Screening for colorectal cancer and other GI cancers. Curr Opin Oncol 1999; 11:305-11.
9. Mandel J S, Bond J H, Church T R, et al. Reducing mortality from colorectal cancer by screening for fecal occult blood. Minnesota Colon Cancer Control Study. N Engl J Med 1993; 328:1365-71.
10. Kronborg O, Fenger C, Olsen J, Jorgensen O D, Sondergaard O. Randomised study of screening for colorectal cancer with faecal-occult-blood test. Lancet 1996; 348:1467-71.
11. Hardcastle J D, Chamberlain J O, Robinson M H, et al. Randomised controlled trial of faecal-occult-blood screening for colorectal cancer. Lancet 1996; 348:1472-7.
12. Towler B, Irwig L, Glasziou P, Kewenter J, Weller D, Silagy C. A systematic review of the effects of screening for colorectal cancer using the faecal occult blood test, Hemoccult. BMJ 1998; 317:559-65.
13. Mandel J S, Church T R, Bond J H, et al. The effect of fecal occult-blood screening on the incidence of colorectal cancer. N Engl J Med 2000; 343:1603-7.
14. Allison J E, Feldman R, Tekawa I S. Hemoccult screening in detecting colorectal neoplasm: sensitivity, specificity, and predictive value. Long-term follow-up in a large group practice setting. Ann Intern Med 1990; 112:328-33.
15. Verne J E, Aubrey R, Love S B, Talbot I C, Northover J M. Population based randomized study of uptake and yield of screening by flexible sigmoidoscopy compared with screening by faecal occult blood testing. BMJ 1998; 317:182-5.
16. Mandel J S, Church T R, Ederer F, Bond J H. Colorectal cancer mortality: effectiveness of biennial screening for fecal occult blood. J Natl Cancer Inst 1999; 91:434-7.
17. Rozen P, Knaani J, Samuel Z. Comparative screening with a sensitive guaiac and specific immunochemical occult blood test in an endoscopic study. Cancer 2000; 89:46-52.
18. Ore L, Hagoel L, Lavi I, Rennert G. Screening with faecal occult blood test (FOBT) for colorectal cancer: assessment of two methods that attempt to improve compliance. European Journal of Cancer Prevention 2001; 10:251-56.
19. Shields H M, Weiner M S, Henry D R, et al. Factors that influence the decision to do an adequate evaluation of a patient with a positive stool for occult blood. Am J Gastroenterol 2001, 96:196-203.
20. Kinzler K W, Vogelstein B. The Genetic Basis of Human Cancer. Toronto: McGraw-Hill, 1998.
21. Sidransky D, Tokino T, Hamilton S R, et al. Identification of ras oncogene mutations in the stool of patients with curable colorectal tumors. Science 1992; 256:102-5.
22. Smith-Ravin J, England J, Talbot I C, Bodmer W. Detection of c-Ki-ras mutations in faecal samples from sporadic colorectal cancer patients. Gut 1995; 36:81-6.
23. Hasegawa Y, Takeda S, Ichii S, et al. Detection of K-ras mutations in DNAs isolated from feces of patients with colorectal tumors by mutant-allele-specific amplification (MASA). Oncogene 1995; 10:1441-5.
24. Koornstra J J, Rokke O, Halvorsen J F, Haug K, Ogreid D. Determination of the activated proto-oncogene (Ki-ras) in feces. A new laboratory analysis for early diagnosis of colorectal cancer. Tidsskr Nor Laegeforen 1995; 115:3266-70.
25. Ratto C, Flamini G, Sofo L, et al. Detection of oncogene mutation from neoplastic colonic cells exfoliated in feces. Dis Colon Rectum 1996; 39:1238-44.
26. Villa E, Dugani A, Rebecchi A M, et al. Identification of subjects at risk for colorectal carcinoma through a test based on K-ras determination in the stool. Gastroenterology 1996; 110:1346-53.

27. Eguchi S, Kohara N, Komuta K, Kanematsu T. Mutations of the p53 gene in the stool of patients with resectable colorectal cancer. Cancer 1996; 77:1707-10.
28. Kohata Y. Detection of K-ras point mutations in the stool of patients with colorectal tumors. Nippon Shokakibyo Gakkai Zasshi 1996; 93:391-7.
29. Nollau P, Moser C, Weinland G, Wagener C. Detection of K-ras mutations in stools of patients with colorectal cancer by mutant-enriched PCR. Int J Cancer 1996; 66:332-6.
30. Deuter R, Muller O. Detection of APC mutations in stool DNA of patients with colorectal cancer by HD-PCR. Hum Mutat 1998; 11:84-9.
31. Puig P, Urgell E, Capella G, et al. Improved detection of K-ras codon 12 mutations in fecal exfoliated cells. Lab Invest 1999; 79:617-8.
32. Ahlquist D A, Skoletsky J E, Boynton K A, et al. Colorectal cancer screening by detection of altered human DNA in stool: feasibility of a multitarget assay panel. Gastroenterology 2000; 119:1219-27.
33. Dong S M, Traverso G, Johnson C, et al. Detecting Colorectal Cancer in Stool With the Use of Multiple Genetic Targets. J Natl Cancer Inst 2001; 93:858-865.
34. Rengucci C, Maiolo P, Saragoni L, Zoli W, Amadori D, Calistri D. Multiple detection of genetic alterations in tumors and stool. Clin Cancer Res 2001; 7:590-3.
35. Doolittle B R, Emanuel J, Tuttle C, Costa J. Detection of the mutated k-ras biomarker in colorectal carcinoma. Exp Mol Pathol 2001; 70:289-301.
36. Boland C R. Genetic pathways to colorectal cancer. Hosp Pract 1997; 32:79-84, 87-96.
37. Kinzler K W, Vogelstein B. Lessons from Hereditary Colon Cancer. Cell 1996; 87:159-170.
38. Tsao J, Shibata D. Further evidence that one of the earliest alterations in colorectal carcinogenesis involves APC. Am J Pathol 1994; 145:531-4.
39. Baker S J, Preisinger A C, Jessup J M, et al. p53 gene mutations occur in combination with 17p allelic deletions as late events in colorectal tumorigenesis. Cancer Res 1990; 50:7717-22.
40. Smith A J, Stern H S, Penner M, et al. Somatic APC and K-ras codon 12 mutations in aberrant crypt foci from human colons. Cancer Res 1994; 54:5527-30.
41. Jen J, Powell S M, Papadopoulos N, et al. Molecular determinants of dysplasia in colorectal lesions. Cancer Res 1994; 54:5523-6.
42. Pretlow T P. Aberrant crypt foci and K-ras mutations: earliest recognized players or innocent bystanders in colon carcinogenesis? Gastroenterology 1995; 108:600-3.
43. Laurent-Puig P, Beroud C, Soussi T. APC gene: database of germline and somatic mutations in human tumors and cell lines. Nucleic Acids Res 1998; 26:269-70.
44. Stryker S J, Wolff B G, Culp C E, Libbe S D, Ilstrup D M, MacCarty R L. Natural history of untreated colonic polyps. Gastroenterology 1987; 93:1009-13.
45. Bond J H. Clinical relevance of the small colorectal polyp. Endoscopy 2001; 33:454-7.
46. Powell S M, Petersen G M, Krush A J, et al. Molecular diagnosis of familial adenomatous polyposis. N Engl J Med 1993; 329:1982-7.
47. van der Luijt R, Khan P M, Vasen H, et al. Rapid detection of translation-terminating mutations at the adenomatous polyposis coli (APC) gene by direct protein truncation test. Genomics 1994; 20:1-4.
48. Ahlquist D A, Harrington J J, Burgart U, Roche P C. Morphometric analysis of the "mucocellular layer" overlying colorectal cancer and normal mucosa: relevance to exfoliation and stool screening. Hum Pathol 2000; 31:51-7.

The invention claimed is:

1. A method of detecting colorectal tumors, comprising:
dividing a test sample of APC alleles isolated from a patient, to form a plurality of aliquots of APC alleles, wherein said aliquots comprise on average between 0 and 20 APC alleles, and wherein the test sample is a body fluid or exudate;
amplifying said APC alleles in said plurality of aliquots to form amplified APC alleles;
transcribing and translating proteins in vitro using said amplified APC alleles as transcription templates;
determining size or composition of said proteins, wherein proteins which differ in size or composition from the protein produced by a wild-type APC allele indicate a mutation in an amplified APC allele which indicates a colorectal tumor in the patient.

2. The method of claim 1 further comprising the step of determining the concentration of APC alleles in the test sample by limiting dilution polymerase chain reaction.

3. The method of claim 1 wherein said proteins are subjected to gel electrophoresis.

4. The method of claim 1 wherein composition of said proteins is determined using mass spectroscopy.

5. The method of claim 1 wherein said aliquots comprise on average between 0 and 10 APC alleles prior to amplification.

6. The method of claim 1 wherein said aliquots comprise on average between 0 and 5 APC alleles prior to amplification.

7. The method of claim 1 wherein said aliquots comprise on average between 0 and 1 APC alleles prior to amplification.

8. The method of claim 1 wherein said aliquots comprise on average between 1 and 20 APC alleles prior to amplification.

9. The method of claim 1 wherein said aliquots comprise on average between 5 and 20 APC alleles prior to amplification.

10. The method of claim 1 wherein said aliquots comprise on average between 10 and 20 APC alleles prior to amplification.

11. The method of claim 1 wherein said aliquots comprise on average between 1 and 5 APC alleles prior to amplification.

12. The method of claim 1 wherein said aliquots comprise on average between 2 and 4 APC alleles prior to amplification.

13. The method of claim 1 wherein size is determined by polyacrylamide gel electrophoresis.

14. The method of claim 1 wherein the step of dividing is performed by diluting the APC alleles to achieve an average number of APC alleles per aliquot of between 0 and 20.

15. The method of claim 1 wherein the step of dividing is performed by diluting the captured APC alleles to achieve an average number of APC alleles per aliquot of between 0 and 5.

16. The method of claim 1 wherein the test sample of APC alleles is isolated from a stool sample of the patient.

17. The method of claim 1 wherein the step of dividing is performed by diluting the test sample.

18. The method of claim 16 wherein at least 500 by of template is amplified.

19. The method of claim 16 wherein at least 750 by of template is amplified.

20. The method of claim 16 wherein at least 1 kb of template is amplified.

21. The method of claim 1 wherein at least a portion of exon 15 is amplified.

22. The method of claim 16 wherein codons 1210 through 1581 of APC are amplified.

23. The method of claim 1 wherein the step of amplifying employs a first and a second set of primers, wherein the first set of primers amplifies a template to which the second set of primers is complementary.

24. The method of claim 1 wherein antibodies to a C-terminal epitope of said proteins are used to determine composition of said proteins.

25. The method of claim 1 wherein antibodies to a C-terminal epitope of said proteins are used to immunodeplete said proteins of full-length proteins.

26. The method of claim 1 wherein antibodies to an N-terminal epitope of said proteins are used to determine size or composition of said proteins.

* * * * *

UNITED STATES PATENT AND TRADEMARK OFFICE
CERTIFICATE OF CORRECTION

| | | |
|---|---|---|
| PATENT NO. | : 7,910,300 B2 | Page 1 of 1 |
| APPLICATION NO. | : 11/703821 | |
| DATED | : March 22, 2011 | |
| INVENTOR(S) | : C. Giovanni Traverso et al. | |

It is certified that error appears in the above-identified patent and that said Letters Patent is hereby corrected as shown below:

Column 24, Claim 18, Line 26:
    Please delete "by" and insert --bp--

Column 24, Claim 19, Line 28:
    Please delete "by" and insert --bp--

Signed and Sealed this
Twenty-fourth Day of January, 2012

David J. Kappos
*Director of the United States Patent and Trademark Office*

UNITED STATES PATENT AND TRADEMARK OFFICE
CERTIFICATE OF CORRECTION

PATENT NO. : 7,910,300 B2
APPLICATION NO. : 11/703821
DATED : March 22, 2011
INVENTOR(S) : C. Giovanni Traverso, Kenneth W. Kinzler and Bert Vogelstein Page 1 of 1

It is certified that error appears in the above-identified patent and that said Letters Patent is hereby corrected as shown below:

In the Specification

Column 1, Lines 6-8, replace "This invention was made using funds from the U.S. government. The government retains certain rights in the invention according to the terms of grants CA57345 and CA62924." with -- STATEMENT OF FEDERALLY SPONSORED RESEARCH This invention was made with government support under CA057345 and CA062924, awarded by the National Institutes of Health. The government has certain rights in the invention. --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*